United States Patent
Bousack et al.

(10) Patent No.: US 8,919,212 B2
(45) Date of Patent: Dec. 30, 2014

(54) INFRARED SENSOR COMPRISING TUNNEL JUNCTION FOR MEASURING THE DEFORMATION OF A MEMBRANE

(75) Inventors: Herbert Bousack, Aachen (DE); Helmut Soltner, Inden (DE); Dirk Mayer, Frechen (DE); Marko Banzet, Geilenkirchen (DE)

(73) Assignee: Forschungszentrum Juelich GmbH, Juelich (DE)

( * ) Notice: Subject to any disclaimer, the term of this patent is extended or adjusted under 35 U.S.C. 154(b) by 86 days.

(21) Appl. No.: 13/807,121

(22) PCT Filed: Jul. 9, 2011

(86) PCT No.: PCT/DE2011/001419
§ 371 (c)(1),
(2), (4) Date: Jan. 11, 2013

(87) PCT Pub. No.: WO2012/010147
PCT Pub. Date: Jan. 26, 2012

(65) Prior Publication Data
US 2013/0205919 A1 Aug. 15, 2013

(30) Foreign Application Priority Data
Jul. 16, 2010 (DE) .................... 10 2010 027 346

(51) Int. Cl.
*G01L 1/24* (2006.01)
*G01N 21/84* (2006.01)
*G01J 5/42* (2006.01)

(52) U.S. Cl.
CPC .. *G01N 21/84* (2013.01); *G01J 5/42* (2013.01)
USPC ...................................... 73/862.634

(58) Field of Classification Search
CPC ......... G01L 5/165; G01B 7/16; G06F 3/0414; G11B 11/08
USPC ..................... 73/760, 849, 862.624
See application file for complete search history.

(56) References Cited

U.S. PATENT DOCUMENTS 4,308,510 A * 12/1981 Yamada et al. ............... 333/194
5,298,748 A 3/1994 Kenny et al.
5,959,200 A * 9/1999 Chui et al. ..................... 73/105
(Continued)

FOREIGN PATENT DOCUMENTS

| DE | 195 20 457 | 12/1996 |
|----|------------|---------|
| DE | 10 2008 018 504 | 10/2009 |
| EP | 2 060 891 | 5/2009 |

OTHER PUBLICATIONS

Kenny T W et al: "Micromachined Infrared Sensors Using Tunneling Displacement Transducers", Review of Scientific Instruments, AIP, Melville, NY, US, vol. 67, No. 1, Jan. 1, 1996, pp. 112-128, XP000554511, ISSN: 0034-6748, DOI: 10.1063/1.1146559 cited in the application figure 2.

*Primary Examiner* — Max Noori
(74) *Attorney, Agent, or Firm* — Jordan and Hamburg LLP (57) ABSTRACT

A sensor array for measuring the deformation of an area caused by a force, comprises a first strip and a second strip arranged in the same plane on the area so as to form a tunnel junction of which at least the first strip is movably arranged on the area so that the gap between the two strips is increased when the area is deformed as a result of the action of the force.

6 Claims, 10 Drawing Sheets

(56) References Cited

U.S. PATENT DOCUMENTS

| | | | |
|---|---|---|---|
| 6,202,495 B1 * | 3/2001 | Zavracky et al. | 73/862.639 |
| 6,318,184 B1 * | 11/2001 | Kimerer, Jr. | 73/772 |
| 6,796,178 B2 * | 9/2004 | Jeong et al. | 73/504.02 |
| 7,218,188 B2 * | 5/2007 | Ma et al. | 333/193 |
| 7,303,703 B2 * | 12/2007 | Hocheng et al. | 264/40.1 |
| 8,461,860 B2 * | 6/2013 | Kim et al. | 324/762.01 |

* cited by examiner

INFRARED SENSOR COMPRISING TUNNEL JUNCTION FOR MEASURING THE DEFORMATION OF A MEMBRANE

BACKGROUND OF THE INVENTION

The invention relates to a sensor array.

A sensor array is known from DE 10 2008 018 504, comprising a deformable membrane in a wall of a measuring chamber that is filled with fluid. The expansion of the fluid that occurs due to heat radiation is transferred to the membrane. The deformation of the membrane is capacitively read out by way of a capacitor on the side of the membrane that is located opposite the fluid. The infrared sensor has the drawback of being comparatively insensitive.

A further sensor array is known from Kenney (Kenny, T W (1996): Micromachined Infrared Sensors Using Tunneling Displacement Transducers. Rev. Sci. Instrum, 67(1), pages 112 to 128). The sensor array is likewise designed as an infrared sensor. The read-out of a signal is assured by way of a tunnel junction. The drawback is that the design of the array is complicated. Large deflections of the membrane can destroy the tunnel junction, so that it is not possible to measure the heat radiation.

It is the object of the invention to provide a robust, yet highly sensitive sensor array for measuring the deformation of an area acted on by a force.

SUMMARY OF THE INVENTION

The sensor array for measuring the deformation of an area caused by a force is characterized in that a first strip S1 and a second strip S2 are arranged on the deformable area in a planar manner, which is to say in the same plane, so as to form a tunnel junction. At least one first strip comprises a section that is not attached to the deformable area. This section is movable and constitutes a pointer. The deformation of the area caused by the action of a force, or the action of pressure, is transferred to the movable section of the first strip, which is to say the section not attached to the area, so that the gap d1 between the two strips S1 and S2 in the region of the tunnel junction is increased due to geometric conditions. The change in the gap and tunneling current caused by the action of the force is directly recorded as a measure of the deformation of the area (uncontrolled operation). As an alternative, feedback control can be employed, in which an electronic circuit actuates a restoring element, for example an electrostatic actuator, and the contact gap or the tunneling current is thus kept constant. In this variant, the reset signal of the feedback control unit is recorded as a measure of the deformation (controlled operation).

The movement of the movable section of the first strip basically takes place out of the plane of the two strips.

The sensor array preferably comprises a first strip S1, which is longer than the second strip S2. This advantageously achieves a high up-conversion ratio of the deformation of the area caused by the action of the force to the deflection of the movable section of the first strip out of the idle position thereof, so that, due to the geometric conditions, even minute deformations of the area lead to very large changes in the gap d1 between the first strip and the second strip in the tunnel junction. This advantageously causes the sensor array to respond to deformations of the area with high sensitivity.

The location of the action of the force and deformation of the area can be directly beneath the two strips S1 and S2, and thus directly in the region of the tunnel junction. Because both strips are arranged on the upper face of the area in the same plane, the deformation of the area due to the action of a force directly affects the gap d1 between the two strips in the tunnel junction at this location. The movable section of the first strip is then raised out of the idle position and separates tangentially away from the area.

The movable, unattached section of the first strip preferably begins in the region of the inflection point W of the bending line of the area. This advantageously causes the first strip to detach as a pointer and separate tangentially away from the deformed area, wherein the separation angle alpha of the pointer relative to the horizontal, which is to say relative to the non-deformed state of the area, takes on the largest angle.

In the case of a circular membrane, which is rigidly clamped at the edge thereof and has the radius R, the locations having the greatest angle alpha relative to the horizontal are found on a circle having the radius $R/\sqrt{3}$ (equation 1) around the center of the membrane. The maximum up-conversion, as the ratio of the contact gap to the maximum deflection of the membrane in the center, is then approximately 2.9.

This type of excitation beneath the tunnel junction of the sensor array is not absolutely essential. Rather, a deflection of the movable part of the first strip S1 is also possible when a deformation of the area takes place by the action of a force outside the region of the tunnel junction, which is to say not directly beneath the two strips S1 and S2.

As described in DE 10 2008 018 504, the sensor array according to the invention can be used to build an infrared sensor that, by comparison, can detect considerably smaller deformations of the membrane as a result of a more sensitive read-out method, and is therefore highly sensitive. Within the scope of the invention, it was found that, compared to the prior art known from Kenney (see above), a robust sensor array is additionally provided, because the strips for the tunnel junction are located in a plane on the surface of the deformable area, so that the deformation of the area will always result in an increase in the gap d1 of the tunnel junction, and thus any collision of the contacts is excluded.

Based on the sensor array, particularly advantageous infrared sensors and deformation sensors, as is the case with strain gauges, are provided as sensor classes.

The strips can be produced using the multi-layer technology known from the prior art. The strips are attached to the surface of the deformable area at one of the ends, respectively. In addition, the second strip S2 can advantageously be completely attached to the upper face of the deformable area.

The longer first strip S1 comprises a section that is not attached to the deformable area and has a free length L2, and a section that is attached to the area and has the length L1. In the case of a circular membrane, which is clamped at the edge thereof and has the radius R, the length L2 can preferably be $R*(1+1/\sqrt{3})$ (equation 2) and the length L1 can preferably be $R*(1-1/\sqrt{3})$ (equation 3). In absolute terms, the free length L2 should be as long as possible. This is achieved by shortening the length of the second strip S2 and/or by a large ratio of L2:L1 in the first strip S1.

The movable section of the first strip preferably starts in the region of the inflection point W of the bending line of the area. This advantageously causes the first strip S1 to detach as a pointer and separate tangentially away from the deformed area, wherein the separation angle alpha of the pointer relative to the horizontal, which is to say relative to the non-deformed state of the area, becomes the greatest.

This advantageously achieves pronounced mobility and a particularly high up-conversion of the change in the gap d1 to d2, which occurred as a result of the deformation, in the tunnel junction. As a result, a highly sensitive sensor array is provided.

The first strip is, or both strips are, made of a material having as high a modulus of elasticity as possible. Iridium, for example, has a modulus of elasticity of 528 GPa. This advantageously results in high rigidity, which is the product of the modulus of elasticity and the axial area moment of inertia of the first strip S1 and directly affects the robustness of the sensor array.

The strips are preferably made of hard, chemically inert material, such as iridium, tantalum, palladium, or tungsten, or an alloy of these materials with chemically inert metals, for example platinum/iridium having various mixing ratios, but also ceramic materials, such as silicon or silicon carbide, if these materials can be metallized in the contact region, or are given metallic properties by way of doping, and form ohmic contact resistances.

The optimal selection of the axial area moment of inertia of the first strip S1 is when the width of the strip is identical to the thickness of the strip. The rigidity is then the same in both main axial directions. For manufacturing reasons, the width of the strip is approximately 10 to 100 times larger than the thickness of the strip. This ensures that the dead weight of the strip leads only to a negligible deflection of the strip.

The resonance frequency $f_R$ of the first strip S1 should be greater than 1 kHz, for example several kHz to MHz, so that oscillations induced by the surroundings do not excite the first strip S1 so as to oscillate the strip and cause high signal noise.

The smallest resonance frequency for a first strip having a rectangular cross-section is obtained from:

$$f_R = 0.56 \cdot \sqrt{\frac{E \cdot I}{m_L \cdot l^4}}, \qquad \text{(equation 4)}$$

where the mass per unit of length of the first strip S1 is $m_L$ and the strip length is l. Specifications for the selection of the geometry of the first strip S1 are obtained for a predetermined length l and a desired high resonance frequency, depending on the material selected. For a contact arm, which is made of iridium and has a width b=50 μm, a height h=1 μm, and a length l=0.355 mm, the lowest resonance frequency results as f=6.2 kHz.

The total length of the first strip S1 can be as high as $R*(1+\sqrt{3})$ (equation 5) for a circular membrane having the radius R.

Thus, the strips S1 and 82 preferably have lengths and materials that can be calculated according to the provided equations.

In one embodiment of the invention, the deformable area is part of a measuring chamber filled with a fluid. This provides a sensor array in a simple manner based on the expansion of the fluid, for example due to incidental heat radiation.

A portion of the wall of the measuring chamber is then designed as a flexible membrane so as to form the area M. An expansion of the fluid causes the membrane to be deformed. The strips, which are arranged on the side of the membrane located opposite the measuring chamber, form the measuring device for detecting the deformation of the membrane. Because at least the first strip can be moved, the gap d1 between the strips S1 and S2 is increased in the region of the tunnel junction.

The sensor array particularly advantageously comprises a window, which is transparent to electromagnetic radiation, in the wall of the measuring chamber. This has an advantageous effect in that a highly sensitive, yet very robust infrared sensor can be provided.

It is conceivable to arrange more than two strips in the same plane on the upper face of the deformable area. Doubling the number of strips will double the tunnel junctions. In this case, two strips are then associated with each other in each case so as to form a tunnel junction. This has an advantageous effect of increasing the effective region in which measurements can be carried out with regard to the deformation of the area, depending on the position of the pairs of strips and formation of the tunnel junctions on the area.

The sensor array comprising the tunnel junction or tunnel junctions can basically be operated using two different methods: these are either a controlled operation using a fixed contact gap, which is assured by a feedback control unit, or without feedback control using a freely variable contact gap.

In the case of junctions having a variable gap, the contact gap is derived from the deflection of the contact arm as the first strip. Depending on the contact gap d1, a variable tunneling current is obtained as the measured variable. This mode of operation is known from the technology of break junctions. The advantage is that no additional control is required. In addition, it is easy to produce.

In the case of junctions having a constant gap, feedback control is employed, wherein a constant tunneling current is ensured at all times with a fixed contact gap between the strips S1 and S2. Like the first mode of operation, this mode is the state of the art in scanning tunneling microscopy.

In a tunneling microscope, the contact gap is likewise controlled. In general, operation with a constant tunneling current or with a constant gap between the tunneling tip and sample is possible. A piezo element, which restores the position of the tunneling tip, is used as an actuator, for example. This technology is the state of the art.

Another use of these junctions could include the measurement of minute deformations of mechanical components, for example when a part of a silicon wafer, on which the junctions were produced, is glued onto the component to be measured, similar to a strain gauge.

The shape of the first and second strips does not necessarily have to be rectangular and also does not have to have a constant cross-section over the length. The strip can, for example, be designed as a triangle so as to increase the resonance frequency.

The invention will be described in more detail hereafter based on exemplary embodiments and the accompanying nine figures, without thereby limiting the invention.

DESCRIPTION OF THE EMBODIMENTS

In the drawings, identical reference numerals denote the following: 1=measuring chamber; 2=transparent window; W=inflection point of the bending line of the area or membrane M.

Figure 1:
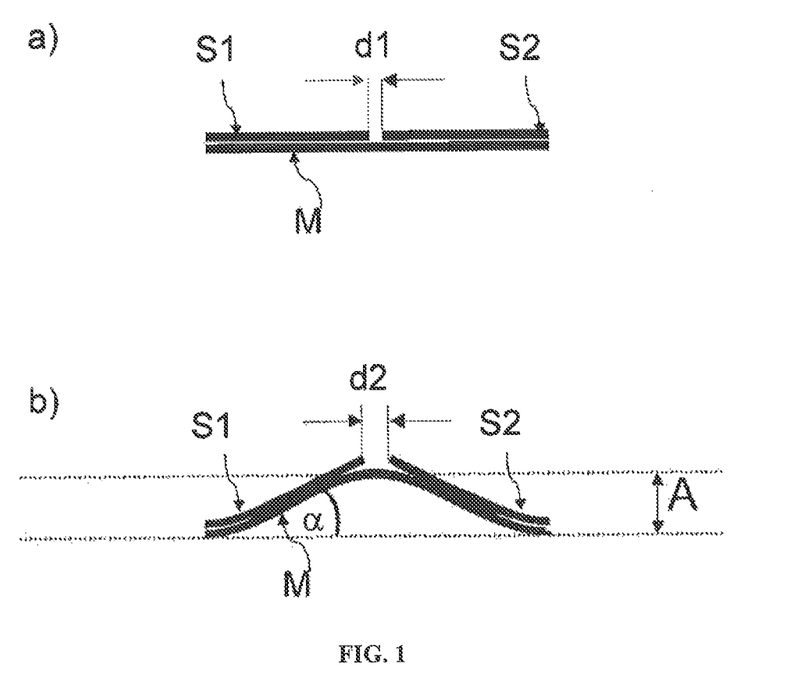
FIG. 1: shows the principle of the sensor array comprising the area M and strips S1 and S2.

FIG. 1 is a rough schematic section of the principle of the sensor array. The two strips S1 and S2 are both located in the same plane on the upper face of the deforming membrane M, which serves as the area. The planar, open arrangement of the strips S1 and S2 considerably simplifies production. In addition, the drawback of a collision of the strips S1 and S2 in the event of an overload, as occurs in the prior art according to Kenney, is prevented, because the array can only increase the gap d1 in the tunnel junction, unlike in Kenney.

According to FIG. 1, strip contacts S1 and S2, which can be electrically contacted and are made of a mechanically hard material, for example iridium, are applied to the membrane M by way of vapor deposition and structuring. When the membrane M is deflected by the maximum amount A, the strips S1 and S2 are raised out of the idle position and the gap d1 increases to d2. In the embodiment shown, the geometry is already improved over the prior art because no collision is possible between the strips S1 and S2. However, this sensor array is still not highly sensitive within the meaning of the invention because the opening of the tunnel junction d2 is smaller than the deflection A to be measured (down-conversion).

Figure 2:
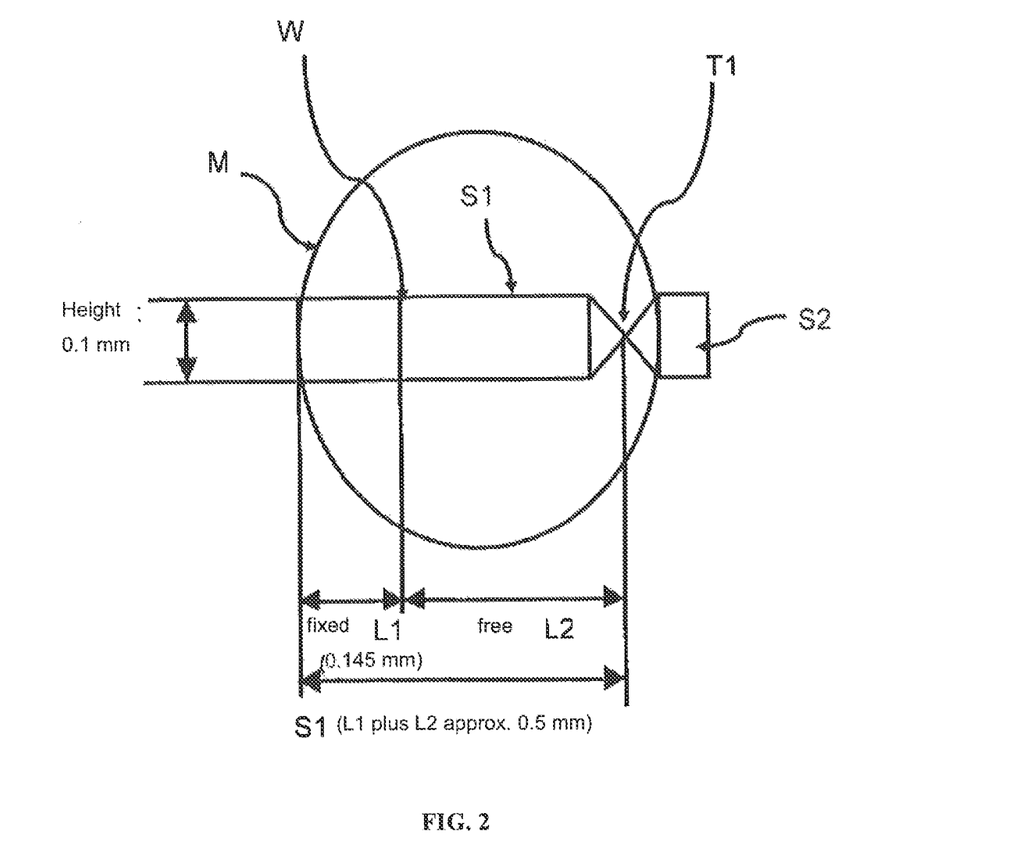
FIG. 2: is an exemplary embodiment of the sensor array comprising a tunnel junction T1.

However, using a suitable geometry, an up-conversion can be achieved as shown in the top view in FIG. 2. To this end, the first strip contact S1 is extended toward the right of the figure to the membrane edge, and the other strip contact S2 is shortened correspondingly. The tips of the two strips are located in the tunnel junction. The free length L2 of the long first strip S1, which is to say the segment that is not connected to the membrane M and is movable, is thus designed to have the longest possible length.

The movable section having the free length L2 begins at the inflection point W of the bending line of the membrane M. Because of this configuration, the long strip S1 separates tangentially away from the deformation of the membrane M caused by the action of a force. As a result, it is easy to achieve a tripling of the up-conversion of the deflection to be measured, which is to say the deflection A is measured at triple the up-conversion d2/A=3; see FIG. 1.

Figure 3:
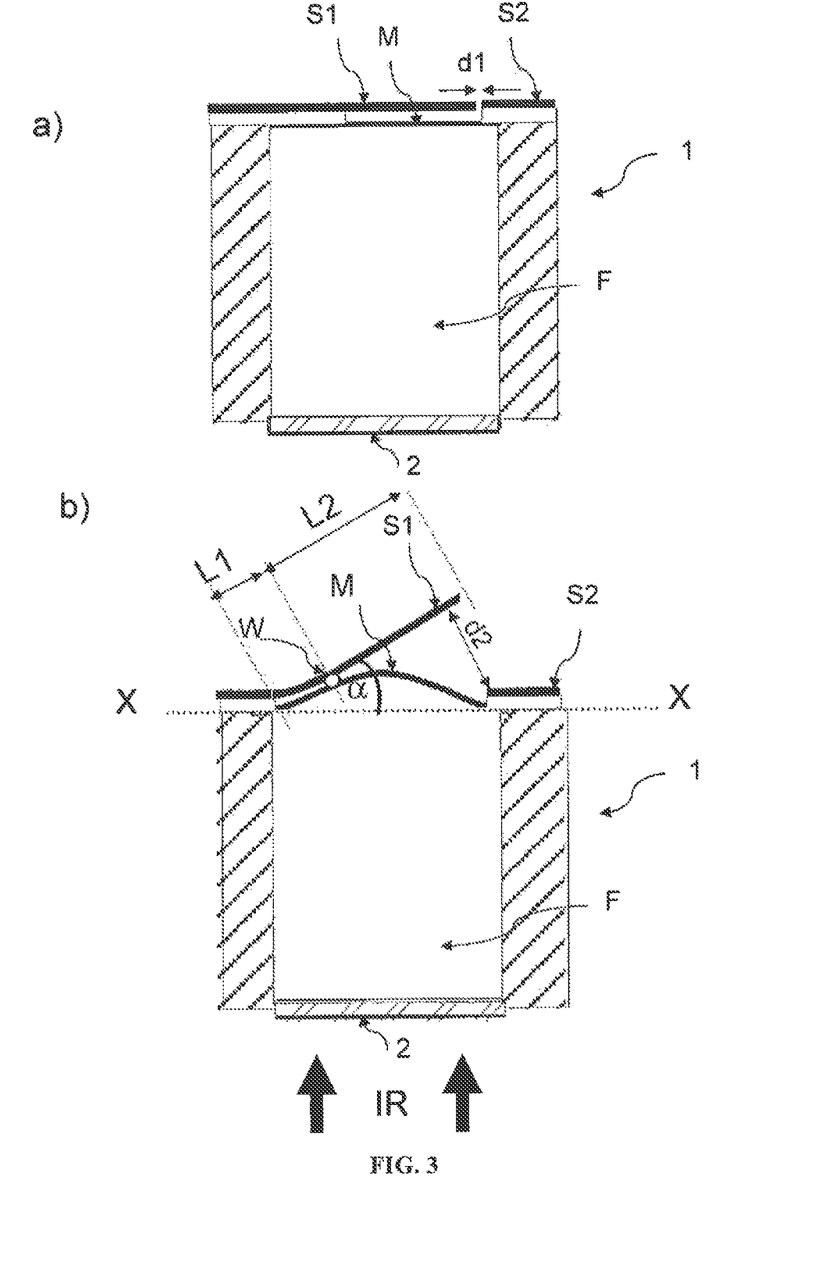
FIG. 3: shows an infrared sensor comprising a measuring chamber 1 and transparent window 2.

FIG. 3 is a schematic section of the integration of this sensor array of FIG. 2 in an infrared sensor. The measuring chamber 1 without the sensor array has the same basic design as in DE 10 2008 018 504. It was produced according to the manner indicated therein and is otherwise made of identical materials. With respect to the production and the materials, the content of DE 10 2008 018 504 shall hereby be considered to be included by reference in the present patent application.

The fluid F in the measuring chamber 1 expands in the chamber 1 after heat radiation enters via the window 2. The change in pressure affects the membrane M, which deforms upward in the figure. Because the free length L2 of the long first strip S1 begins exactly at the inflection point W of the bending line of the membrane M, tangential separation of the first strip S1 away from the membrane M is possible, whereby the gap d1 (FIG. 3a) increases to d2 (FIG. 3b). This advantageously causes the first strip to detach as a pointer and separate tangentially away from the deformed area, wherein the separation angle alpha of the pointer relative to the horizontal (illustrated by X-X), which is to say relative to the non-deformed state of the area, becomes as large as possible.

On the other hand, the principle, as shown in FIG. 2, can of course also be applied to different configurations and sensor arrays, such as strain gauges.

Production of the Tunnel Junction:

Depending on the mode of operation, a different design of the tunnel junction is obtained. In general, all proposed embodiments can be implemented in multi-layer technology, which is known to the person skilled in the art from the prior art.

Figure 4:
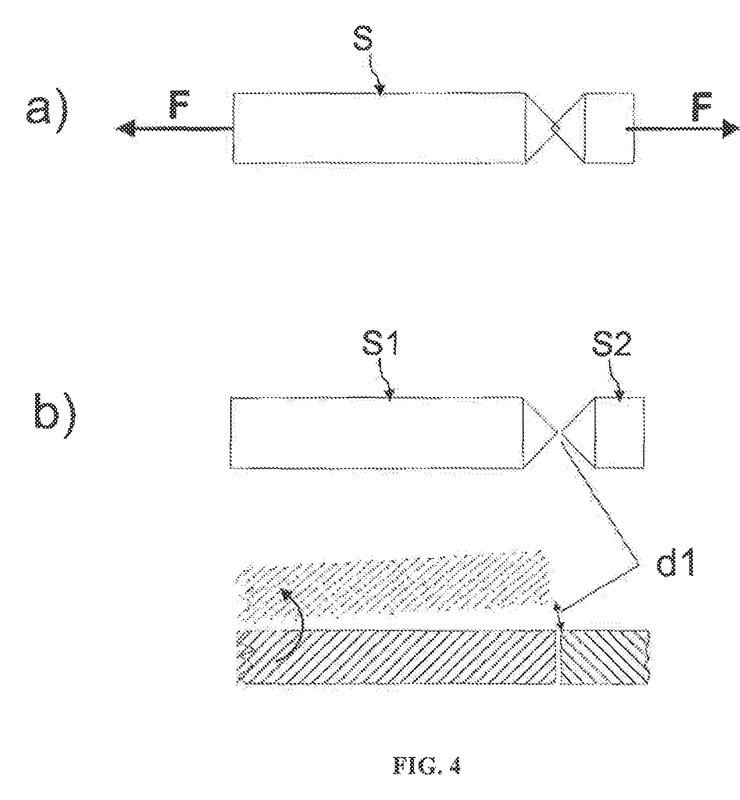
FIG. 4: shows a production method with a break junction (F=force)

In order to produce the tunnel junction, it is important to implement the remaining connecting point, refer to FIG. 4a, as thin as possible. The actual production of the tunnel junction is carried out similar to that of break junctions, by breaking the connecting point. So as to apply the force F to this connecting point, a measuring chamber 1, as shown in FIG. 3b, is subjected to a pressure, whereby the membrane deforms and the connecting point of the contacts is torn open by the expansion of the membrane M, forming the strips S1 and S2. The required pressure can vary slightly for every sensor and must be experimentally determined by gradually increasing the pressure. A control step with regard to a breakage that occurred can be carried out by way of a resistance measurement via the contacts during the pressure application.

FIG. 4a shows a top view onto the strip just before breakage. The upper part of FIG. 4b shows the tunnel junction already opened at the strips S1 and S2 with the gap d1. The bottom part shows a rough schematic section of the process when pressure is applied to the strip S.

The production of a tunnel junction using strips S1 and S2, which should be operated with a constant gap between each other by way of a feedback control unit, is more complex because an actuator must be integrated as the final control element.

Figure 5:
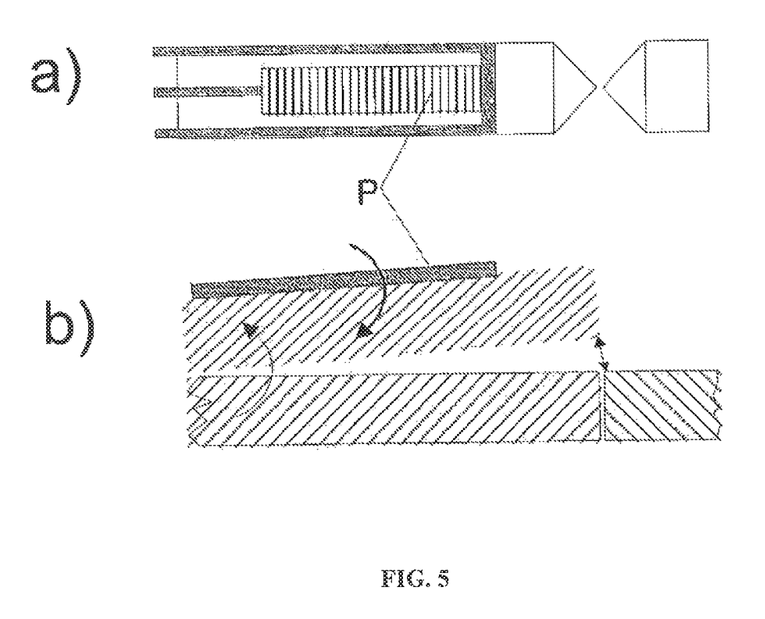
FIG. 5: shows feedback control by way of a piezo element P.

FIG. 5 shows one option for operating the sensor array. Here, a piezoelectric layer P is applied to the long strip S1. When the strip S1 lifts off tangentially as a result of a pressure load on the membrane M (not shown) and the contact gap d1 is increased to d2, a voltage is applied to the piezoelectric layer P, causing the layer to expand. The production of piezoelectric layers P and the actuation thereof is the state of the art. Because of the fixed connection to the upper contact face, the contact is bent downward, similar to a bimorph, until the target value of the tunneling gap is again achieved. The target value of the contact gap is measured via the tunneling current that develops, which can be 1.5 nA, for example, for the working point. When the target value has been reached, the piezoelectric layer is not expanded further.

Figure 6:
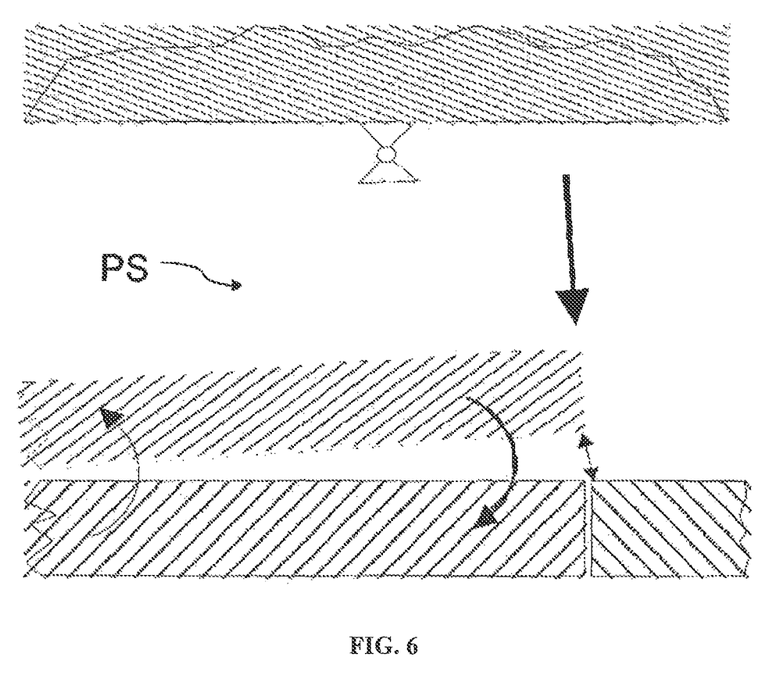
FIG. 6: shows feedback control by way of a piezo element stack PS.

Another design of feedback control by way of a piezo element is shown in FIG. 6. Here, piezoelectric layers or a piezo crystal are applied to the first strip S1 so that the change in length of the layer or of the crystal, during actuation by way of a voltage, is sufficient to restore an additional deflection of the strip beyond the target value. With a piezoelectric coefficient of expansion of approximately $5 \times 10^{10}$ mN and an applied voltage of 2 V, the change in length that is obtained is sufficient to compensate for a gap of the tunnel junctions of 1 nm. At a customary relative change in length of 0.1% of the piezoelectric layer, this results in a height for the layer of approximately 1 μm. When implemented as a layer, various deposition methods, for example PECVD (plasma-enhanced chemical vapor deposition), MOCVD (metal organic chemical vapor deposition), or sputtering can be employed. The design and production of such layer systems is the state of the art.

Figure 7:
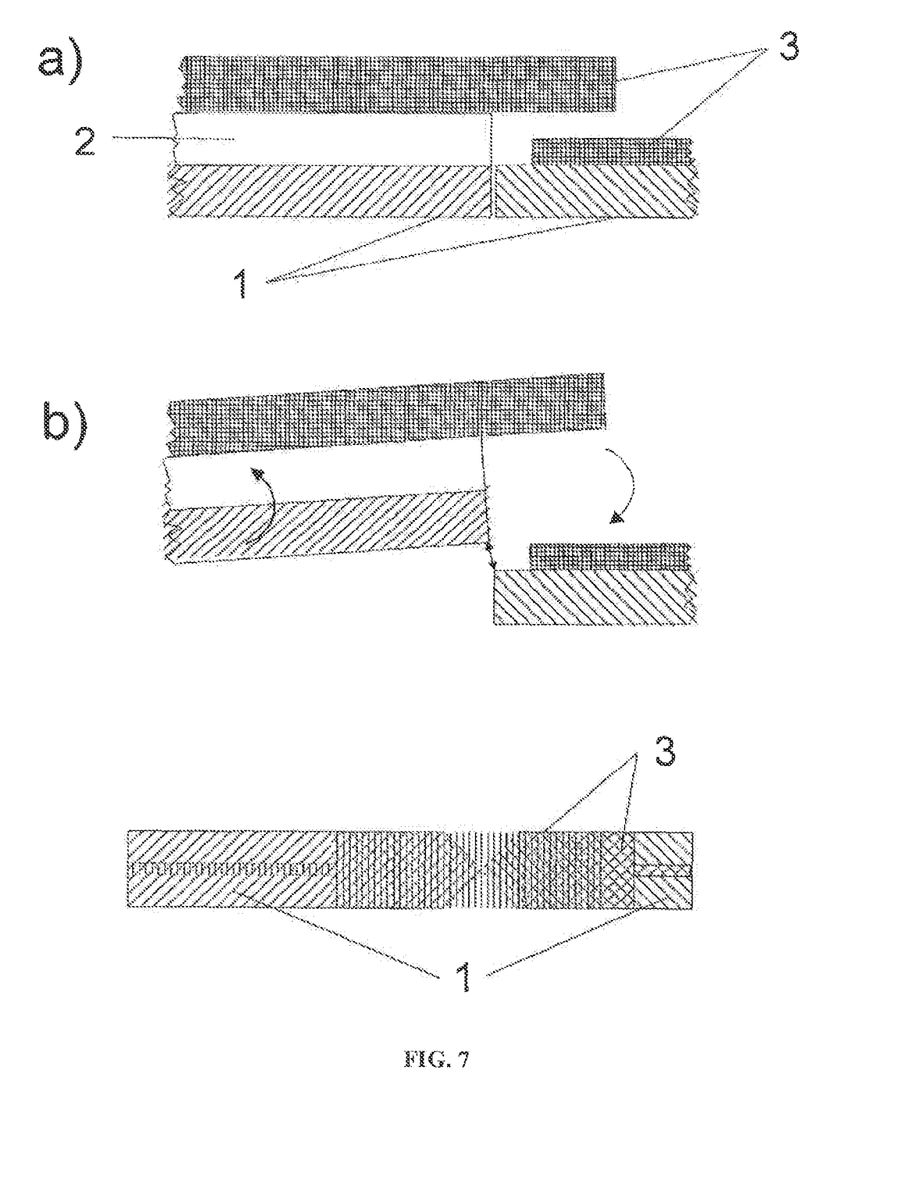
FIG. 7: shows feedback control by way of electrostatic actuators.

A representative illustration comprising an electrostatic actuator is shown in FIG. 7. An insulator layer 2, on which a metallic layer 3 is disposed, is provided on the long strip S1.

The same layer 3 is provided on the short contact S2. Both layers 3 form plates of the electrostatic actuator. During a deflection of the contact beyond the target value, one of the plates is positively charged and the other plate is negatively charged. The target value is adjusted again by the restoring force that develops. The function of an electrostatic actuator is the state of the art. A multi-layer process is required to produce the same, which is known to the person skilled in the art from the prior art.

Figure 8:
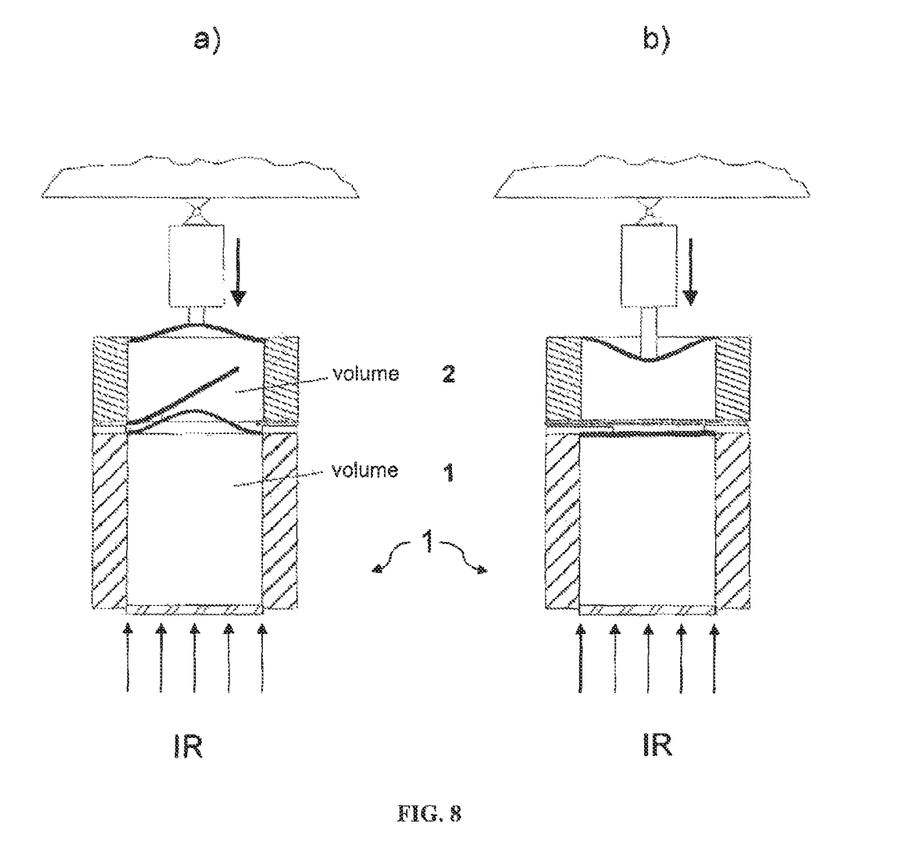
FIG. 8: shows feedback control by way of an actuator and a balancing chamber.

Another option for controlling the gap between the electrodes of a break junction to a constant value is establishing pressure equalization; refer to FIG. 8. For this purpose, a compensation cell having the volume 2 is applied to the sensor cell having the volume 1, for example, by way of gluing. The heat radiation impinging on the volume 1 (arrows) causes this volume to expand and, as a result, the pressure to rise in the chamber having the volume 1. The increase in pressure in turn results in a force, which causes the membrane M to bend. The bending of the membrane can be compensated for by applying a complementary counter pressure in the volume 2. The compensation cell having the volume 2 is likewise provided with a membrane, which can be bent into the interior region by an actuator. As a result of the bending of the membrane, the volume 2 of the compensation chamber decreases and the pressure rises. The feedback control assures that the same pressure exists between volumes 1 and 2 and that the bending of the break junction is kept constant.

The controlled operation, as shown in FIGS. 5 to 8, is disclosed, for example, in column 7, line 37 to column 8, line 9 of U.S. Pat. No. 5,298,748, in conjunction with FIG. 5, which is hereby incorporated by reference in the present patent application.

Figure 9:
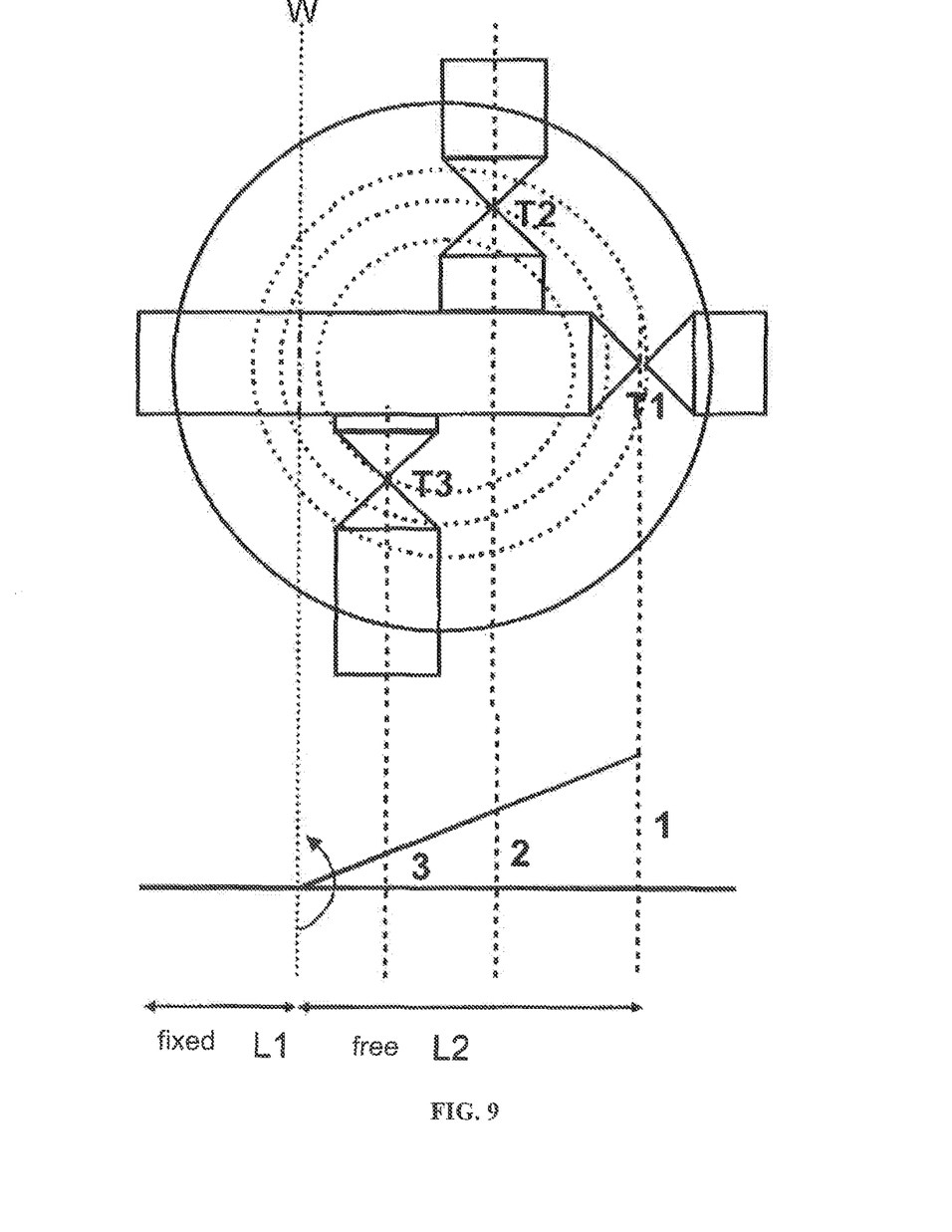
FIG. 9: is an exemplary embodiment of the sensor array comprising three tunnel junctions T1 to T3.

FIG. 9 shows another embodiment of a sensor array according to the invention. A drawback of uncontrolled contacts having a variable gap is that a tunneling current is no longer present if the deflection is too strong, and consequently, the sensor function is compromised. This drawback can be decreased by several lateral tunnel junctions T2. T3; refer to FIG. 9. By adjusting the gaps of the contacts around the center of the membrane, the deflections 1, 2, 3 can be adjusted so that the working range is increased. W denotes the inflection point.

Figure 10:
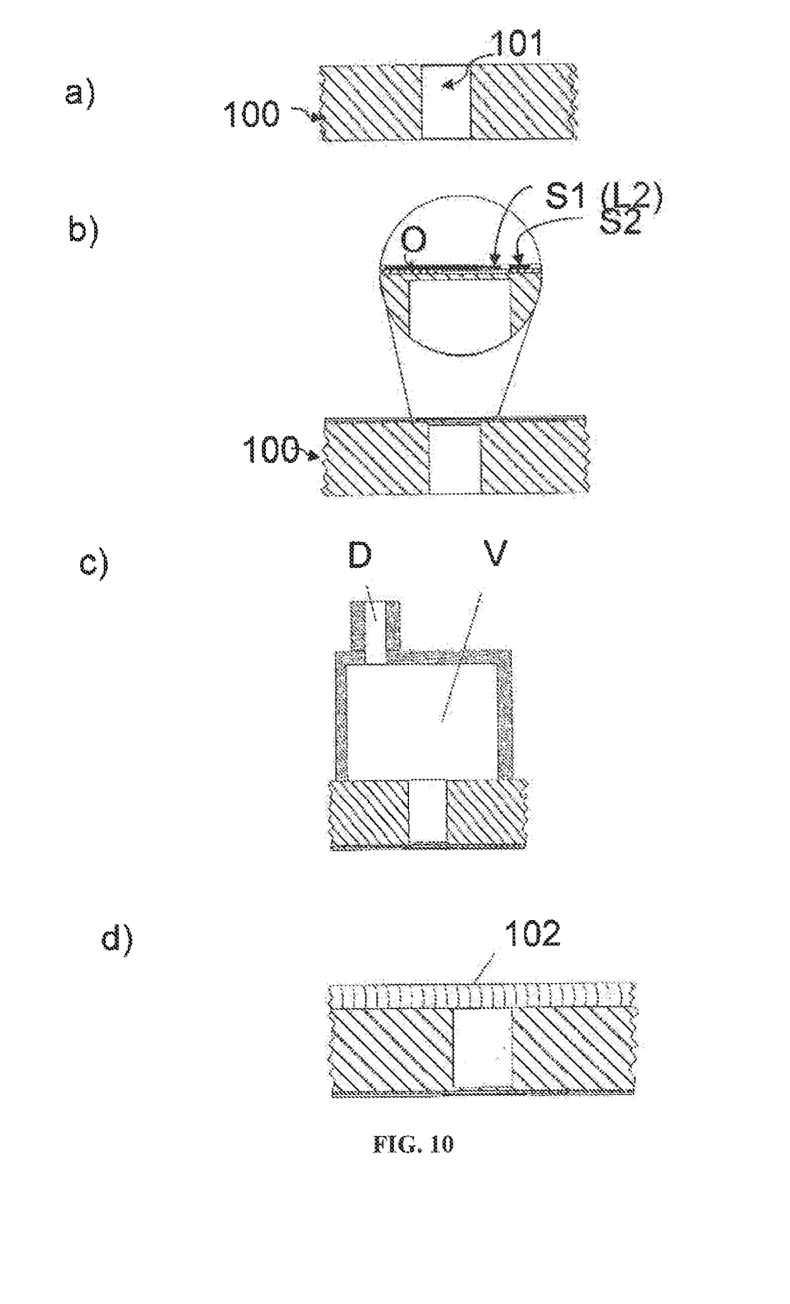
FIG. 10: shows a production method.

So as to produce an IR sensor comprising planar tunnel junctions, proceed based on the following process steps (FIG. 10).

Production of the cell for receiving a fluid (FIG. 10*a*)): proceeding from a silicon wafer 100 having a thickness of 0.7 mm, a cell 101 having a diameter of 0.5 mm is etched in one side of the wafer using deep reactive etching (DRIE), and an anisotropic etching process. The depth of the cell is selected so that only a bottom remains as the membrane, having a thickness of 1 μm.

Production of the planar tunnel junctions: A sacrificial layer O made of chromium, for example, having a thickness of 200 to 300 nm is applied to the other side of the wafer, which has not been machined, refer to FIG. 10*b*, by way of vapor deposition using physical vapor deposition (PVD). A layer having a thickness of 1 μm, made of iridium, for example, is deposited thereon by way of PVD. Thereafter, the planar tunnel junctions are structured by way of a lift-off process. The tips of the strips, which should have the smallest possible connecting area (layer height×connecting width), are structured using an electron beam writer. Connecting widths of 50 to 100 nm are advantageous. The sacrificial layer between the silicon and the tunnel junction is then removed by way of wet-chemical etching, so that the first strip S1 having the free length L2 made of iridium is produced in keeping with the hand length. Up until now, however, the two strips S1 and S2 of the junction are still joined by a connecting area.

So as to break apart the tips of the junctions by a force, the wafer is subjected in the cells to a pressure so that the membrane curves (refer to FIG. 10*c*). As a result of this curving, the junction is subjected to a force at the connecting point, which causes the contacts to break when the force is increased up to a breaking force. The necessary pressure can only be determined experimentally.

The cells can be filled with a gaseous fluid or a liquid. If filled with a gas other than air, this must be done, for example, in a glove box or a volume V that is closed in an appropriate manner, using an adjustable overpressure. If filled with a liquid, care must only be taken that no gas bubbles remain in the cell. This is ensured by a pressure connection D.

After filling, the cells are closed off by gluing on a window 102 that allows infrared radiation to pass; refer to FIG. 10*d*.

The invention claimed is:

1. A sensor array for measuring the deformation of an area caused by a force, comprising:
    a first strip and a second strip arranged in the same plane on an area so as to form a tunnel junction of which at least the first strip is movably arranged on said area so that a gap between the two strips is increased when said area is deformed by the action of the force; and
    wherein said area is part of a measuring chamber filled with a fluid.

2. The sensor array according to claim 1, wherein a wall of the measuring chamber is designed as a flexible membrane so as to form said area.

3. The sensor array according to claim 2, comprising a window, which is transparent to electromagnetic radiation, in the wall of the measuring chamber.

4. The sensor array according to claim 1, wherein the first strip is longer than the second strip.

5. A sensor array according to claim 1, wherein the first strip comprises a movable section that is not attached to said area and has a free length, and a section that is attached to said area and has an attached length.

6. The sensor array according to claim 5, wherein the free length is greater than the attached length.

* * * * *